United States Patent [19]

Murphy

[11] Patent Number: 5,565,622

[45] Date of Patent: Oct. 15, 1996

[54] REDUCED SOLVENT SOLID PHASE EXTRACTION

[75] Inventor: Gregory E. Murphy, Erial, N.J.

[73] Assignee: Hewlett-Packard Co., Legal Dept., Palo Alto, Calif.

[21] Appl. No.: 306,551

[22] Filed: Sep. 15, 1994

[51] Int. Cl.$^6$ ............................................. G01N 13/00
[52] U.S. Cl. ............................................. 73/61.55
[58] Field of Search ........................... 73/61.55, 864.87

[56] References Cited

U.S. PATENT DOCUMENTS

| | | | |
|---|---|---|---|
| 4,615,226 | 10/1986 | DiNuzzo et al. | 73/864.87 |
| 4,680,201 | 7/1987 | Hjerten | 427/230 |
| 4,808,449 | 2/1989 | McAlister | 428/34.1 |
| 5,038,708 | 8/1991 | Wells et al. | 118/318 |
| 5,212,000 | 5/1993 | Rose et al. | 428/34.7 |
| 5,322,608 | 6/1994 | Karger et al. | 204/299 |
| 5,387,526 | 2/1995 | Garner et al. | 436/169 |
| 5,431,821 | 7/1995 | Olesik et al. | 210/635 |

FOREIGN PATENT DOCUMENTS

WO91/15745  4/1991  WIPO.

OTHER PUBLICATIONS

*Dynamics of Organic Compounds Extraction from Water Using Liquid–Coated Fused Silica Fibers,* Derek Louch, Safa Motlagh and Janusz Pawliszyn, Analyticalytical Chemistry, vol. 64, No. 10, May 15, 1992, pp. 1187–1199.
*Your Link to Success—HP 7686 PrepStation Cartridges and Consumables,* Copyright 1993 Hewlett–Packard Company, Printed in U.S. Apr. 1993, pub. #5091–6881EUS.
*Discover New Effciency and Economy with Just In–Time Sample Preparation,* Copyright 1992 Hewlett–Packard Company, Printed in U.S. Oct. 1992, pub. (43)5091–5893E.
*Solid–Phase Extraction For Chromatography Sample–Prep,* Copyright 1993 Alltech Associates, Inc., Jan., 12, 1994, Bulletin #202, pp. 2, 3, 12.
Mol et al, Use of an open–tubular trapping . . . , J Chromatography, 630 (1993) 201–212.
Moi et al, Use of Open–Tubular Column . . . , J. High Resolution, vol. 16, Jul. 93, 413–418.

*Primary Examiner*—Hezron E. Williams
*Assistant Examiner*—Jay L. Politzer
*Attorney, Agent, or Firm*—Richard F. Schuette

[57] ABSTRACT

A simplified method for solid phase extraction of components of interest from a sample employing a syringe in which the inner surface of the cannula or needle is at least partially coated with a stationary phase such that aspirating the sample into the needle results in adsorption of the components of interest into the stationary phase. Aspiration of a solvent may be employed for removing the components of interest from the stationary phase for direct injection into a chromatographic instrument, or the components of interest may be removed by thermal desorption, wherein the needle is placed in the injection port of the chromatographic instrument and heated.

10 Claims, 3 Drawing Sheets

REDUCED SOLVENT SOLID PHASE EXTRACTION

FIELD OF THE INVENTION

The invention relates generally to the preparation of samples for introduction into a gas chromatograph. Specifically, this invention relates to an improved method for solid phase extraction (SPE) of components of interest from a liquid sample.

BACKGROUND OF THE INVENTION

Chromatography is a preferred method for the analysis of samples. In particular, gas chromatography is particularly good for environmental samples as impurities and contaminates in most environmental are not complex molecules. More complex molecules necessitate the use of supercritical fluid chromatography or liquid chromatography. Prior to the introduction of a sample into a chromatographic instrument, the sample must be prepared such that components of interest can be extracted from the sample.

Solid phase extraction (SPE) is a technique which utilizes a flow-through chamber that contains a large number of small inert silica particles each coated with a stationary phase material. The liquid sample is flushed through the cartridge and the components of interest diffuse into the stationary phase coating. A solvent having a high solubility factor for the components of interest is then flushed through the cartridge, thereby dissolving and carrying away the components of interest for analysis. The Hewlett-Packard 7686 PrepStation System is an example of a system that provides for fully automated SPE, including filtering, heating and evaporating. After sample preparation is complete, components of interest are typically dissolved into a solvent and temporarily stored in a sample vial. A syringe is typically employed for aspirating the solvent containing components of interest and injecting them into an appropriate chromatographic apparatus. The syringe may be operated manually or automatically using automatic injection apparatus. See, for example, U.S. Pat. No. 4,615,226 entitled "Apparatus and Method for Introducing Solutes into a Stream of Carrier Gas of a Gas Chromatograph" issued on Oct. 7, 1986 to DiNuzzo et al.

A technique for carrying out Solid Phase Microextraction (SPME) without the use of solvent is disclosed in International Application Number PCT/CA91/00108 entitled "Method and Device for Solid Phase Microextraction and Desorption" by Janusz B. Pawliszyn. A solid fused silica fiber coated with a secondary phase is attached to the plunger mechanism of a standard syringe such that the fiber can be extended from inside the hollow syringe needle. The needle is inserted through a septum and into a vial. The plunger is depressed so that the fiber will extend into the sample such that the components of interest diffuse into the stationary phase coating until equilibrium is reached, whereupon, the fiber is withdrawn into the needle and the needle is withdrawn from the sample vial. Continuous mixing of the sample during the diffusion step shortens the period required for equilibrium. The needle is then inserted through a septum and into injection port of a gas chromatograph such that the components of interest are then thermally desorbed and cryofocused on the column.

The quantity of components of interest that are absorbed is directly related to the surface area and thickness of the stationary phase. Increasing film thickness to increase capacity has the detrimental effect of slowing the rate of absorption. Thus, a problem with SPME is its limited flexibility regarding film thickness. SPME is problematic due to the inherent fragility of fused silica when extended through a syringe needle, and because the stationary phase coating on the outer surface of the fused silica is unprotected when extended.

There is a need for a robust sample preparation technique which reduces or eliminates the amount of solvent required for sample preparation.

SUMMARY OF THE INVENTION

The invention is a simplified method for solid phase extraction of components of interest employing a syringe in which the-inner surface of the cannula or needle is at least partially coated with a stationary phase. The invention may be practiced manually using a syringe typically used for manual injections, or automatically using an automatic injector in which the syringe has a needle coated with a stationary phase.

In a first embodiment of the present invention suitable for manual applications the needle is inserted into a sample vial containing a liquid sample with components of interest. A quantity of sample is aspirated through the needle, into the barrel of the syringe and then dispensed back into the sample vial. The process of aspiration and dispensing the sample is continued until the components of interest diffuse into the stationary phase coating on the inner surface of the needle and preferably an equilibrium is reached. (Rapid aspiration and dispensing may be effected to optionally ensure that the components of interest contact the stationary phase coating and to provide a mixing action of the sample in the sample vial to minimize the time required for equilibrium.) A final dispense stroke dispenses substantially all of the sample back into the sample vial. The needle is then withdrawn from the sample vial and inserted directly into an injection port of a chromatographic instrument for thermal desorption type injection.

In a second embodiment of the present invention suitable for direct injection, an amount of solvent sufficient to cover the stationary phase coating is aspirated from the solvent vial. The components of interest then desorb from the stationary phase coating into the solvent. Since a relatively small amount of solvent is employed, the concentration of components of interest is very high. The needle is then inserted into the injection port of a chromatographic instrument for injection.

In a third embodiment of the present invention suitable for fully automated extraction and injection, an automatic injector is employed having a needle coated with a stationary phase, and a sample vial tray assembly (hereinafter "tray") for indexing a sample vial into position below the injection needle. The automatic injector inserts the needle into the sample vial and aspirates the sample into the barrel of the syringe. The sample is then dispensed back into the sample vial. This process is repeated several times until the components of interest diffuse into the stationary phase coating, after which the sample is dispensed completely from the syringe.

The components of interest may be injected utilizing known thermal desorption and cryofocusing techniques. Alternatively, the needle may be lowered into a solvent vial to aspirate enough solvent to cover the stationary phase coating in the needle. After waiting a period of time sufficient for the components of interest in the coating to desorb into the solvent, the solvent containing components of interest is injected into the injection port of a chromatographic instrument.

Therefore, it is a feature and an advantage of the invention to provide a flexible extraction technique compatible with both thermal desorption and direct injection of highly concentrated components of interest.

An advantage of the invention is the relatively small amount solvent required for direct injection.

Another advantage of the invention is the fact that it can be performed manually with only the addition of a stationary phase coating to at least part of the inside surface of the needle or by an automatic injection device with minor modification of the injection sequence. The inside diameter and length of the needle may be varied to permit accurate variation of the amount of stationary phase coating.

The invention may be embodied in a robust design that protects and locates the stationary phase on the inner surface of the syringe needle.

DESCRIPTION OF THE PREFERRED EMBODIMENT

Figure 1:
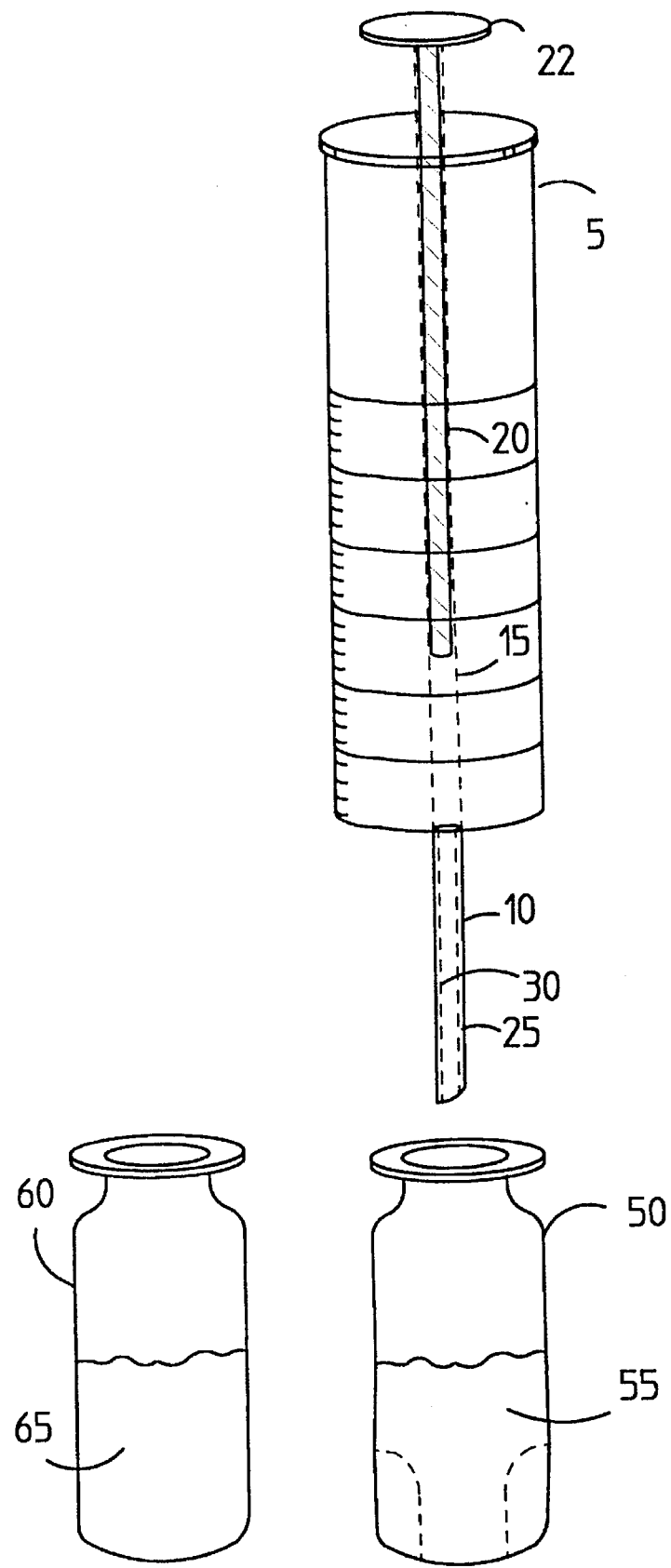
FIG. 1 is a plan view of the invention and illustrates a syringe on which the inner surface of the needle thereof comprises a stationary phase coating.

The invention may be embodied in a manual mode as illustrated in FIG. 1 in which an injector syringe 5 comprises a hollow injector needle 10, a barrel 15 and a plunger 20 slidably mounted within the barrel 15. The plunger 20 includes a handle 22 such that the syringe can be operated manually. The needle 10 has an inner surface 25 coated with a stationary phase coating 30. In the preferred embodiment, the entire inner surface of the needle is coated. However, depending on the stationary phase coating, a partial coating may be employed as long as it provides for sufficient extraction of the components of interest.

The invention provides for a sample vial 50 containing a liquid sample 55. The injector needle is inserted into the sample vial 50 and the sample 55 is aspirated into the barrel 15 and redispensed back into the sample vial 50. Aspiration and redispensing is repeated until the components of interest have the opportunity to diffuse into a stationary phase coating 30. The repeated dispensing back into the sample vial may be done with a rapid dispense stroke to assist in stirring and mixing of the diluted, aspirated sample with the remaining sample in the sample vial. A rapid aspiration stroke may also be used for maximizing the contact of the sample with the inner surface. Once the components of interest have diffused into the coating and reached an equilibrium condition, the needle tip is raised to above the level of the sample in the sample vial and several rapid dispense strokes are employed to ensure that no sample is left in the needle.

Figure 2:
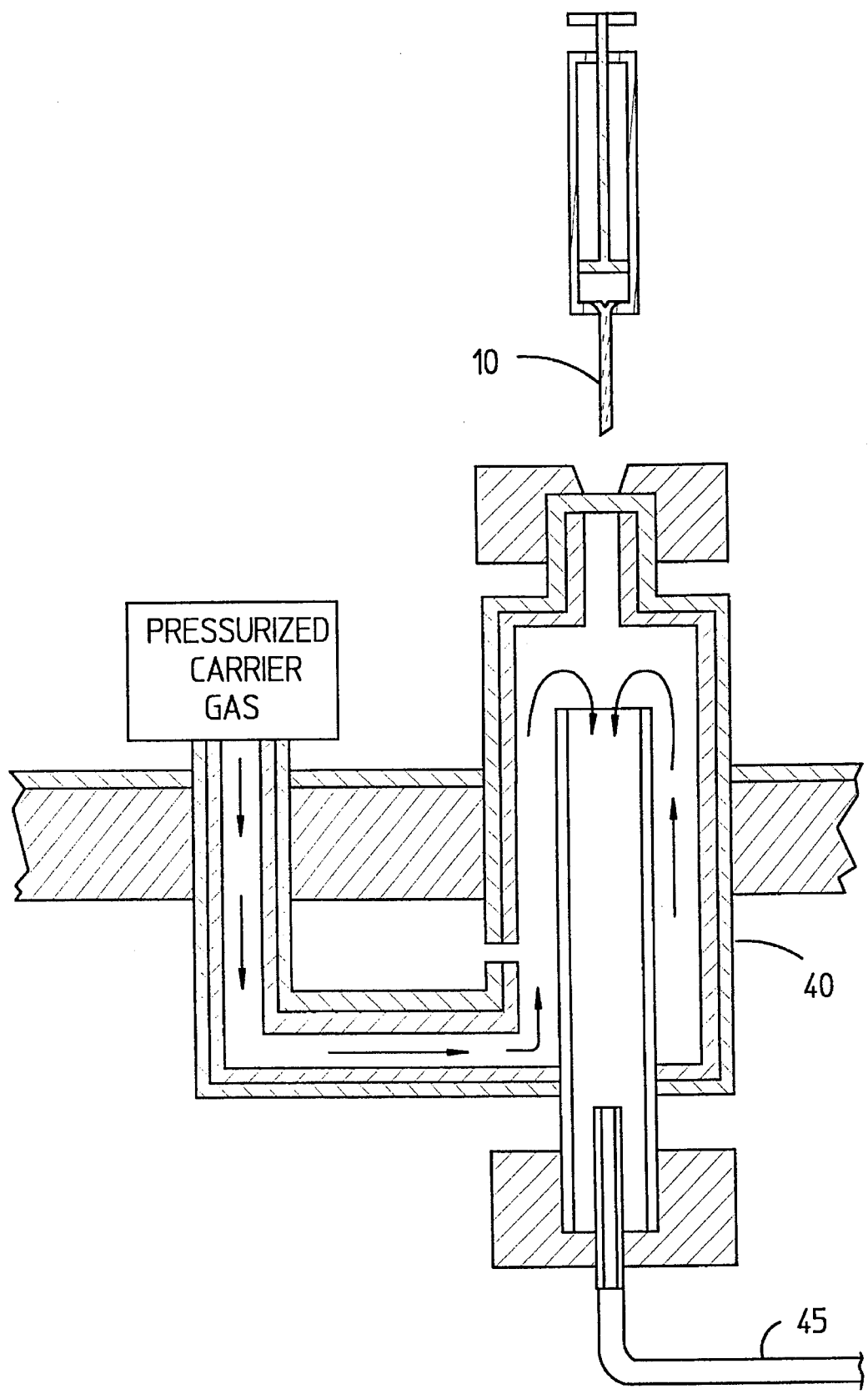
FIG. 2 is a plan view of the invention and illustrates a syringe and an injection port of a gas chromatograph.

The needle 10 is inserted into the injection port 40 of an analytical instrument as illustrated in FIG. 2 such that the components of interest previously absorbed into the stationary phase coating 30, can be thermally desorbed using known techniques. In particular, the temperature in the injection port 40 is maintained at a temperature greater than the highest boiling point of the components of interest such that they desorb from the stationary phase coating. Cryotrapping, a known technique for cooling a downstream portion of the injection port 40, may be employed to trap all of the components of interest on the head of the column 45 prior to the actual chromatographic separation.

In an alternative embodiment, direct injection may be accomplished by inserting the needle 10 into a solvent vial 60 containing a takeup solvent 65 such that a small amount of solvent sufficient to fill the needle 10 without going into the barrel 15 is aspirated. The components of interest deposited into the coating 30 desorb into the solvent. Since there is only a very small volume of solvent present in the needle, the concentration of desorbed components of interest is very high. Heat may be applied to the needle 10 to assist in the desorption. The needle 10 is then retracted completely from the solvent vial 60 and the syringe 5 is then employed for injecting the solvent containing components of interest into an injection port of an analytical instrument for analysis.

If contamination of the solvent remaining in the solvent vial is a concern, a high recovery vial containing only a small amount of sample should be employed. Proper cleaning of the solvent and or sample vial may include rinsing with deionized water, methanol or an appropriate non-polar solvent prior to use.

Figure 3:
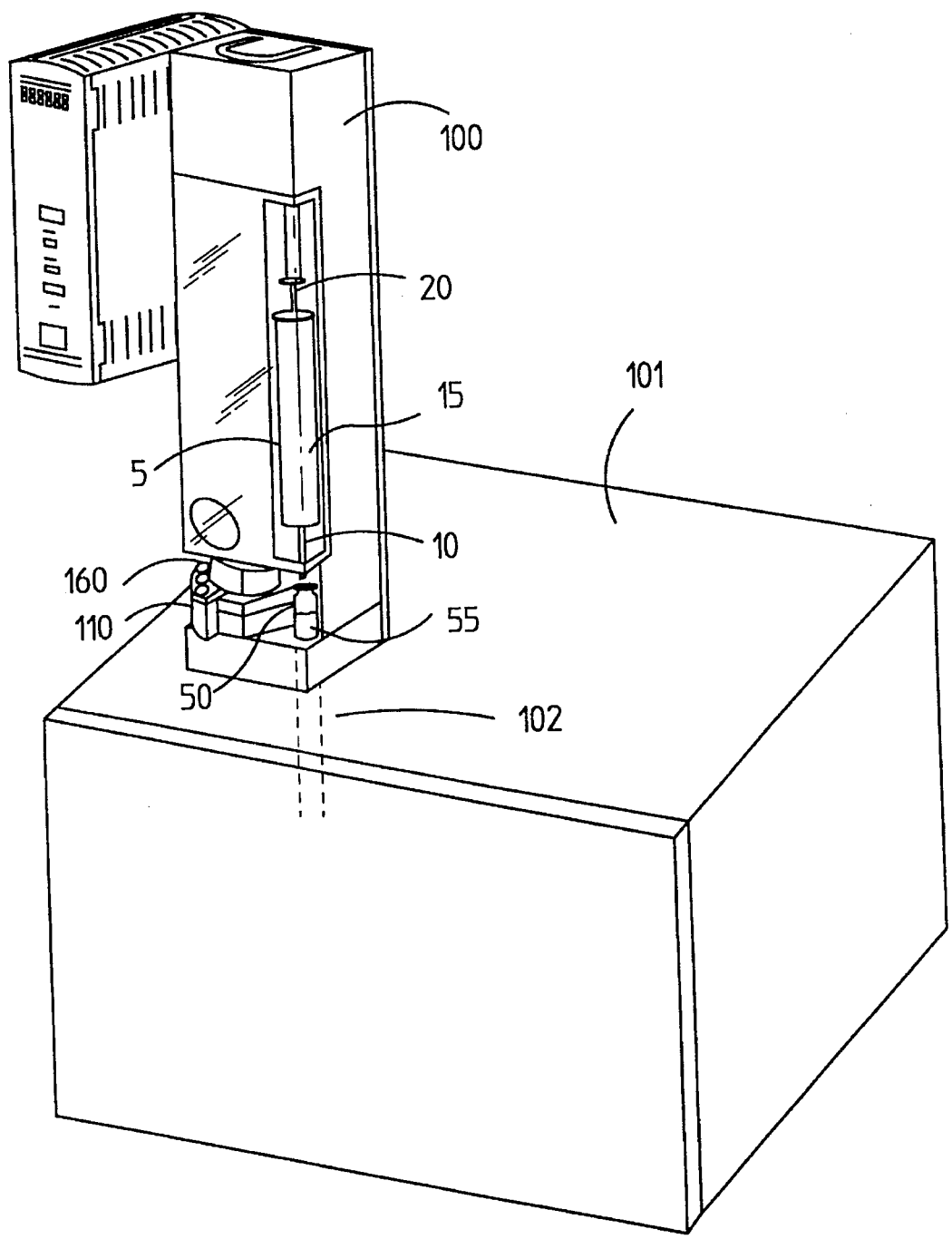
FIG. 3 is a plan view of the invention and illustrates an automatic injector employing a needle in which the inner surface comprises a stationary phase coating.

FIG. 3 illustrates an alternative embodiment in which an automatic injector 100 mounted on top of a gas chromatograph 101 is employed for automatically performing sample preparation such that injections can be made directly into the injection port 102. The automatic injector 100 includes the syringe 5 previously described for manual injections. In particular, the syringe 5 has a hollow injector needle 10, a barrel 15 and a plunger 20 slidably mounted within the barrel 15. The injector needle 10 has an inner surface coated with a stationary phase coating.

A three position tray 110 indexes sample vial 150 into a position below the injector needle 10. The needle 10 is then inserted into the sample vial and sample 55 is aspirated in and out of the needle. After the components of interest have had the opportunity to diffuse into the stationary phase coating, the remaining sample is dispensed from the needle 10. A thermal desorption type injection may now be performed by indexing the sample vial out of position under the needle and inserting the needle into the injection port 102 of the analytical instrument.

Alternatively, direct injection may be accomplished by indexing a solvent vial 160 containing a takeup solvent under the needle 10. A small amount of solvent sufficient to fill the needle 10 without going into the barrel 15 is aspirated. The components of interest deposited into the coating 30 desorb into the solvent. Since there is only a very small volume of solvent present in the needle, the concentration of desorbed components of interest is very high. Heat may be applied to the needle 10 to assist in the desorption. The needle 10 is then retracted completely from the solvent vial 160 and the solvent vial is indexed out of position from under the needle 10. The needle 10 is then inserted into the injection port and the plunger 20 actuated such that the solvent containing components of interest are injected.

Although certain embodiments of the present invention have been set forth above and described in detail, these embodiments are meant to provide examples of the usefulness of the present invention and explain its operation and are not meant to limit the invention. Upon review of this specification, those of skill in the art will realize numerous variations, modifications and other applications for the invention disclosed. Accordingly, reference should be made to the appended claims in order to determine the scope of the present invention.

I claim:

1. A method for solid phase extraction of components of interest from a liquid sample utilizing an injector syringe, said liquid sample being held in a sample vial, said injector syringe comprising a hollow needle having an inner surface coated with a stationary phase, said method comprising the steps of:

inserting the needle into said sample vial; and aspirating the sample in and out of the needle such that components of interest have the opportunity to be adsorbed on said stationary phase coating; and inserting the needle into the injection port of a chromatographic instrument; and thermally desorbing the components of interest into the injection port.

2. A method for solid phase extraction of components as claimed in method claim 1, further comprising the step of:

dispensing all of the sample out of the needle after the components of interest have had the opportunity to reach equilibrium with the stationary phase coating and prior to thermal desorption.

3. A method for solid phase extraction of components as claimed in method claim 1, further comprising the step of:

cryotrapping the thermally desorbed components of interest in the injection port prior to chromatographic separation.

4. A method for solid phase extraction of components of interest from a liquid sample utilizing an injector syringe, said sample being held in a sample vial, said syringe further comprising a barrel with a plunger slidably mounted within the barrel, a hollow needle having an inner surface extending to the end of the barrel opposite the plunger, said inner surface further comprising a stationary phase coating, said method comprising the steps of:

inserting the needle into said sample vial; and aspirating the sample in and out of the barrel by actuating the plunger in a back and forth motion such that components of interest have the opportunity to be adsorbed on said stationary phase coating; and dispensing all of the sample out of the syringe barrel; and inserting the needle into a solvent vial containing a solvent having an affinity to the components of interest; and aspirating an amount of solvent sufficient to cover said stationary phase coating by pulling the plunger back slightly; and waiting an amount of time sufficient for the components of interest to dissolve into the solvent; and inserting the needle into the injection port of a chromatographic instrument; and injecting the sample by pushing the plunger all the way forward.

5. A method for solid phase extraction of components of interest from a liquid sample being held in a sample vial, in which a solvent having the ability to dissolve said components of interest is held in a solvent vial, and an automatic injector is employed for automatically actuating an injector syringe, said syringe further comprising a barrel with a plunger slidably mounted within the barrel, a hollow needle having an inner surface extending to the end of the barrel opposite the plunger, said inner surface further comprising a stationary phase coating, said method comprising the steps of:

transporting a sample vial to a position beneath the syringe; and inserting the needle into said sample vial; and aspirating the sample into the barrel by pulling the plunger back; and dispensing the sample back into the sample vial by pushing the plunger back in; and repeating the aspiration and dispensing of the sample until the components of interest have had an opportunity to diffuse into said stationary phase coating; and dispensing the sample back into the sample vial; and transporting the sample vial away from the syringe and transporting a solvent vial to a position beneath the syringe; and inserting the needle into the solvent vial containing a solvent having an affinity to the components of interest; and aspirating said solvent into the needle; and waiting a period of time sufficient for the contaminants in the coating to desorb into the solvent; and injecting the solvent containing contaminates into the injection port of a chromatographic instrument.

6. The method for solid phase extraction of components of interest from a liquid sample being held in a sample vial as claimed in method claim 5, said step of transporting further comprising employing a tray having a plurality of positions to hold the sample vial and the solvent vial.

7. An apparatus for performing solid phase extraction of a sample containing components of interest, said sample being held in a sample vial and a solvent having the ability to dissolve the components of interest being held in a solvent vial, comprising:

an injector syringe, further comprising a barrel and a plunger slidably within the barrel, the plunger having a handle extending from one end of the barrel; and a hollow needle having an inner surface extending to the end of the barrel opposite the plunger, said inner surface further comprising a stationary phase coating;

wherein, the needle is inserted into the sample vial and the sample is aspirated in and out of the barrel through the needle by pulling the handle back and forth until the components of interest have had an opportunity to diffuse into the stationary phase coating, and wherein, the sample is dispensed completely from the barrel, and wherein the needle is pulled out of the sample vial and inserted into a solvent vial and a small amount of solvent sufficient to fill only the needle is aspirated into the syringe such that components of interest dissolve into said solvent, and wherein, said solvent is then injected into a chromatographic instrument.

8. An apparatus for performing solid phase extraction of a sample containing components of interest as claimed in apparatus claim 7, wherein said needle may be replaced with a different needle having different internal and external dimensions.

9. An apparatus for performing solid phase extraction of a sample containing components of interest as claimed in apparatus claim 7, further comprising an automatic injector for holding said injector syringe, wherein said automatic injector automatically moves said plunger and handle back and forth to aspirate the sample and inject the solvent containing components of interest.

10. An apparatus for performing solid phase extraction of a sample containing components of interest as claimed in apparatus claim 7, further comprising a tray having a plurality of positions for holding vials and for moving said vials into position below said injector syringe.

* * * * *